(12) United States Patent
Tanguay et al.

(10) Patent No.: US 10,940,057 B2
(45) Date of Patent: Mar. 9, 2021

(54) DEVICE FOR THE JELLIFICATION OF A WATER-BASED FLUID, USE AND METHOD FOR TRANSFORMING THE WATER-BASED FLUID INTO A SOLID GEL, AND A METHOD FOR MANUFACTURE OF SAID DEVICE

(71) Applicant: Hy-Industrie Inc., Drummondville (CA)

(72) Inventors: Eric Tanguay, Candiac (CA); Eric Pelletier, St-Felix de Kingsey (CA)

(73) Assignee: HY-INDUSTRIE INC., Drummondville (CA)

( * ) Notice: Subject to any disclaimer, the term of this patent is extended or adjusted under 35 U.S.C. 154(b) by 106 days.

(21) Appl. No.: 16/396,249

(22) Filed: Apr. 26, 2019

(65) Prior Publication Data
US 2019/0328589 A1 Oct. 31, 2019

Related U.S. Application Data

(60) Provisional application No. 62/663,514, filed on Apr. 27, 2018.

(30) Foreign Application Priority Data

Jul. 27, 2018 (CA) .............................. CA 3012654

(51) Int. Cl.
| | |
|---|---|
| *A61F 13/551* | (2006.01) |
| *A61M 1/00* | (2006.01) |
| *A61F 13/15* | (2006.01) |
| *B32B 27/08* | (2006.01) |
| *B32B 27/20* | (2006.01) |
| *B32B 27/30* | (2006.01) |
| *A61F 13/53* | (2006.01) |

(52) U.S. Cl.
CPC ...... *A61F 13/551* (2013.01); *A61F 13/15211* (2013.01); *A61M 1/0001* (2013.01); *B32B 27/08* (2013.01); *B32B 27/20* (2013.01); *B32B 27/306* (2013.01); *B32B 27/308* (2013.01); *A61F 2013/530007* (2013.01); *A61F 2013/530569* (2013.01); *A61F 2013/530591* (2013.01); *B32B 2262/04* (2013.01); *B32B 2307/726* (2013.01)

(58) Field of Classification Search
CPC .............. A61F 13/551; A61F 13/15211; A61F 2013/530591; A61F 2013/530569; A61F 2013/530007; A61M 1/0001; B32B 27/08; B32B 27/20; B32B 27/306; B32B 27/308; B32B 2262/04
See application file for complete search history.

(56) References Cited

U.S. PATENT DOCUMENTS 5,387,207 A * 2/1995 Dyer et al. .............. A61F 13/15
604/369

* cited by examiner

*Primary Examiner* — Michael C Miggins
(74) *Attorney, Agent, or Firm* — Schaffer, Schaub & Marriott, Ltd.

(57) ABSTRACT

A device for the jellification/absorption of a water-based fluid, said device comprising a) at least one member comprising at least one absorption material and at least one jellifying agent, and b) at least one container, wherein the at least one jellifying agent is adapted to react with the water-based fluid to form a gel; wherein the at least one member is contained within the at least one container, and wherein the at least one container is made, at least in part, of a water-soluble material. A method for the manufacture of the device and a use of the device.

20 Claims, 8 Drawing Sheets

DEVICE FOR THE JELLIFICATION OF A WATER-BASED FLUID, USE AND METHOD FOR TRANSFORMING THE WATER-BASED FLUID INTO A SOLID GEL, AND A METHOD FOR MANUFACTURE OF SAID DEVICE

CROSS REFERENCE TO A RELATED APPLICATION

The present patent application claims the priority of U.S. provisional application Ser. No. 62/663,514, filed Apr. 27, 2016, the content of which is incorporated herein in its entirety.

FIELD OF THE INVENTION

The invention relates to a device for the jellification of a water-based fluid. Also, the invention relates to a use and a method for transforming the water-based fluid into a solid gel. Also, the invention relates to a method for the manufacture of said device.

PRIOR ART

It is known in the art to use jellifying materials for transforming a water-based fluid into a solid gel. However, handling of the jellifying materials may be laborious, and/or the efficiency of the solid gel formation may be unsatisfactory.

Also, when the water-based fluid is a contaminated fluid (e.g. domestic water-based fluids, industrial water-based fluids and/or biological water-based fluids), disposal of said fluids cannot be poured into a sewage drain. Disposal of such fluids is strongly regulated to prevent and/or minimize safety hazards. More particularly, examples of contaminated biological fluids may be blood, secretions, saliva, vomit, urine, feces, etc. Optionally, such biological fluids may be collected with a suction apparatus provided with a suction canister.

Therefore, there is a strong need for a device allowing to efficiently transform a water-based fluid into a solid gel, without drawbacks of the prior art, especially regarding the handling, efficiency of the solid gel formation, safety and/or regulatory requirements.

The Applicant has surprisingly discovered a new device allowing, at least in part, to overcome and/or reduce drawbacks of the prior art.

More particularly, the Applicant has surprisingly discovered that a device comprising in a mix of at least one absorption material and at least one jellifying agent in a container that is made at least in part of a water-soluble paper or at least one film of a water soluble polymer, improves handling and/or storage of said mix.

Also, the Applicant has surprisingly discovered that the above-mentioned mix contained in the above-mentioned container, greatly accelerates and/or improves the speed and capacity of absorption of a water-based fluid, and its transformation into a solid gel within the absorption material.

Also, the Applicant has surprisingly discovered that providing one or several openings in the container further substantially reduce the total time required by the water-based fluid to dissolve the water-soluble paper or the at least one film of water-soluble polymer, and being absorbed by the absorption material and jellified therein.

SUMMARY OF THE INVENTION

A possible embodiment of the invention relates to a device for the jellification/absorption of a water-based fluid, said device comprising:
  a) at least one member comprising at least one absorption material and at least one jellifying agent, and
  b) at least one container,
wherein the at least one jellifying agent is adapted to react with the water-based fluid to form a gel;
wherein the at least one member is contained within the at least one container, and
wherein the at least one container is made, at least in part, of a water-soluble material.

Another possible embodiment of the invention relates to the device defined hereinabove, wherein the at least one absorption material is a fluffy material, wherein the at least one jellifying agent is in the form of particles, and wherein the fluffy material and the particles are mixed together to form the mixture, and then said mixture is shaped to form said at least one member.

Another possible embodiment of the invention relates to the device defined hereinabove, wherein the at least one member is further provided with at least one support material.

Another possible embodiment of the invention relates to the device defined hereinabove, wherein the at least one member corresponds to at least one layer of the mixture, and the at least one support material corresponds to at least one layer of the support material, preferably at least two layers of the support material, cooperating with the at least one layer of the mixture to form a multilayer assembly.

Another possible embodiment of the invention relates to the device defined hereinabove, wherein when two layers of the support material are present, each of said layers of the support material cooperates with the at least one layer of the mixture to form a multilayer assembly (i.e. a sandwich like structure), the at least one layer of the mixture being positioned between the two layers of the support material.

Another possible embodiment of the invention relates to the device defined hereinabove, wherein the multilayer assembly is a compressed multilayer assembly.

Another possible embodiment of the invention relates to the device defined hereinabove, wherein the at least one layer of the support material comprises at least one fabric of natural and/or synthetic fibers, and/or comprises at least one sheet of paper. Preferably, according to another possible embodiment of the invention, the at least one layer of the support material is made of at least one fabric of natural and/or synthetic fibers, and/or is made of a sheet of paper.

Another possible embodiment of the invention relates to the device defined hereinabove, wherein an example of natural fibers may be cotton, an example of synthetic fibers may be acrylic or polyethylene fibers, and an example of the sheet of paper may be a sheet of tissue paper.

Another possible embodiment of the invention relates to the device defined hereinabove, wherein when more than one of the at least one layer of the support material is present, they can comprise or be made of the same material or of different material. Preferably, according to another possible embodiment of the invention, they are made of the same material.

Another possible embodiment of the invention relates to the device defined hereinabove, wherein the multilayer assembly has a determined shape such as for example a stick shape, a disk shape, etc.

Another possible embodiment of the invention relates to the device defined hereinabove, wherein the determined shape is preferably a stick shape.

Another possible embodiment of the invention relates to the device defined hereinabove, wherein the fluffy material is a fluff of synthetic and/or natural fibers, and the particles of the at least one jellifying agent are particles of the at least one superabsorbent polymer.

Optionally, according to another possible embodiment of the invention, the fluffy material may consist of recycled synthetic and/or natural fibers (e.g. industrial waste products), or may be a mix of the recycled synthetic and/or natural fibers, and virgin synthetic and/or natural fibers.

Another possible embodiment of the invention relates to the device defined hereinabove, wherein the fluffy material is a fluff of cellulosic fibers, and wherein the particles of the at least one superabsorbent polymer are particles of at least one sodium acrylate copolymer.

Another possible embodiment of the invention relates to the device defined hereinabove, wherein the cellulosic fibers may consist of recycled cellulosic fibers, virgin cellulosic fibers, or may be a mix of recycled cellulosic fibers and virgin cellulosic fibers.

Another possible embodiment of the invention relates to the device defined hereinabove, wherein the fluffy material is a recycled fluffy material containing an amount of at least one jellifying agent.

Another possible embodiment of the invention relates to the device defined hereinabove, wherein the recycled fluffy material may be recycled cellulosic fibers obtained from industrial rejects of personal hygiene products such as incontinence briefs, baby diapers, women hygiene products, etc. Optionally, according to another possible embodiment of the invention, the recycled cellulosic fibers may further comprise particles of the at least one superabsorbent polymer (e.g. particles of at least one sodium acrylate copolymer), and optionally some impurities such as plastic materials.

Another possible embodiment of the invention relates to the device defined hereinabove, wherein the particles of the at least one superabsorbent polymer may be obtained from industrial waste.

Another possible embodiment of the invention relates to the device defined hereinabove, wherein the particles of the at least one jellifying agent have an average diameter size varying from 50 µm to 500 µm; wherein the at least one absorption material represents from 2% by weight to 99% by weight, preferably from 40% by weight to 60% by weight, more preferably about 50% by weight, of the total weight of the at least one absorption material and the particles of the at least one jellifying agent; and wherein the particles of the at least one jellifying agent represents from 1% by weight to 98% by weight, preferably from 40% by weight to 60% by weight, more preferably about 50% by weight, of the total weight of at least one absorption material and the particles of the at least one jellifying agent.

Another possible embodiment of the invention relates to the device defined hereinabove, wherein the at least one container is made of at least one sheet of a water-soluble paper and/or of at least one film of a water-soluble polymer.

Another possible embodiment of the invention relates to the device defined hereinabove, wherein the at least one film of a water-soluble polymer has an inner surface, an outer surface and at least one opening allowing the water-based fluid to flow from the outer surface to the inner surface, and then contact the at least one absorption material and the at least one jellifying agent. Preferably, the at least one film of a water-soluble polymer may be provided with a plurality of openings.

Another possible embodiment of the invention relates to the device defined hereinabove, wherein the at least one water-soluble sheet of paper has an inner surface, an outer surface and at least one opening allowing the water-based fluid to flow from the outer surface to the inner surface, and then contact the at least one absorption material and the at least one jellifying agent. Preferably, the at least one water-soluble sheet of paper is provided with a plurality of openings.

Another possible embodiment of the invention relates to devices as defined hereinabove and provided with at least one opening, wherein said at least one opening are of any size and/or shape appropriate to allow water-based fluid to flow therethrough. As a non-limiting example, the at least one opening may have a diameter of about 0.045 inch. Also, preferably when a plurality of openings is provided, they can be distributed (randomly or according to a given pattern) on the surface of the device. As a non-limiting example, lines of openings may be provided with openings at about 0.25 inch from each other.

Another possible embodiment of the invention relates to the device defined hereinabove, wherein the water-soluble material is a film of polyvinyl alcohol (PVA) or a sheet of tissue paper.

Another possible embodiment of the invention relates to the device defined hereinabove, wherein the film of the water-soluble material is a film of polyvinyl alcohol.

Another possible embodiment of the invention relates to the device defined hereinabove, wherein the at least one container is made of at least one film of the water-soluble polymer that is further thermo-sealable.

Another possible embodiment of the invention relates to the device defined hereinabove, wherein said at least one container defines a pouch, a sachet, a bag or an envelope.

Another possible embodiment of the invention relates to a method for the manufacture of the device defined hereinabove, wherein said method comprises a step of introducing at least one member into the at least one container; or a step of forming said container around the at least one member.

Another possible embodiment of the invention relates to the method defined hereinabove, wherein several of the at least one member (e.g. a stack of 6) are in the container.

Another possible embodiment of the invention relates to the method defined hereinabove, wherein the at least one absorption material is a fluffy material, and wherein the at least one jellifying agent is in the form of particles, said method further comprising a step of mixing the fluffy material with the particles of the at least one jellifying agent to obtain a mixture, and a step of forming the mixture into the at least one member.

Another possible embodiment of the invention relates to the method defined hereinabove, wherein when the at least one member is further provided with at least one layer of a support material cooperating with the at least one member to form a multilayer assembly, said method further comprising a step of contacting the at least one member with the at least one layer of the support material.

Another possible embodiment of the invention relates to the method defined hereinabove, further comprising a step for cutting the multilayer assembly into a desired shape Another possible embodiment of the invention relates to the method defined hereinabove, further comprising a step of compressing and optionally heating the multilayer assembly to provide a compressed assembly.

Another possible embodiment of the invention relates to the method defined hereinabove, further comprising steps of compressing and heating the multilayer assembly to provide a compressed assembly. Preferably, the steps of compressing and heating are simultaneously carried out in a calender.

Another possible embodiment of the invention relates to the method defined hereinabove, further comprising a step for cutting the compressed multilayer assembly into a desired shape.

Another possible embodiment of the invention relates to the method defined hereinabove, wherein the at least one member corresponds to at least one layer of the mixture, and wherein the at least one layer of the support material cooperates with at least one layer of the mixture to form a multilayer assembly.

Another possible embodiment of the invention relates to the method defined hereinabove, wherein the at least one member corresponds to at least one layer of the mixture, and wherein the at least one layer of the support material comprises two layers of the support material cooperating with at least one layer of the mixture to form a multilayer assembly. Preferably, according to another possible embodiment of the invention, the at least one layer of the mixture is positioned between the two layers of the support material.

Another possible embodiment of the invention relates to the method defined hereinabove, wherein the at least one member corresponds to at least one layer of the mixture, and wherein the at least one layer of the support material cooperates with at least one layer of the mixture to form the compressed multilayer assembly.

Another possible embodiment of the invention relates to the method defined hereinabove, wherein the at least one member corresponds to at least one layer of the mixture, and wherein the at least one layer of the support material comprises two layers of the support material, each layer of the support material cooperating with the at least one layer of the mixture to form the compressed multilayer assembly, and wherein the at least one layer of the mixture is positioned between the two layers of the support material. Preferably, according to another possible embodiment of the invention, the at least one layer of the mixture is positioned between the two layers of the support material.

Another possible embodiment of the invention relates to the method defined hereinabove, wherein the at least one layer of the support material comprises at least one fabric of natural and/or synthetic fibers, and/or comprises at least one sheet of paper.

Another possible embodiment of the invention relates to the method defined hereinabove, wherein the at least one layer of the support material is made of at least one fabric of natural and/or synthetic fibers, and/or is made of a sheet of paper.

Another possible embodiment of the invention relates to the method defined hereinabove, wherein an example of natural fibers may be cotton, an example of synthetic fibers may be acrylic or polyethylene fibers, and an example of paper may be a sheet of tissue paper.

Another possible embodiment of the invention relates to the method defined hereinabove, wherein when more than one layer of the support material is present, they can comprise or be made of the same material or of different material. Preferably, according to another possible embodiment of the invention, they are made of the same material.

Another possible embodiment of the invention relates to the method defined hereinabove, wherein the multilayer assembly has a determined shape such as for example a stick shape, a disk shape, etc.

Another possible embodiment of the invention relates to the method defined hereinabove, wherein the determined shape is preferably a stick shape.

Another possible embodiment of the invention relates to the method defined hereinabove, wherein the fluffy material is a fluff of synthetic and/or natural fibers, and the particles of the at least one jellying agent are particles of the at least one a superabsorbent polymer. Of course, any kind of particles of superabsorbent polymers well known to a person skilled in the art can be used.

Optionally, according to another possible embodiment of the invention, the fluffy material may consist of recycled synthetic and/or natural fibers (e.g. industrial waste products), or may be a mix of the recycled synthetic and/or natural fibers, and virgin synthetic and/or natural fibers.

Another possible embodiment of the invention relates to the method defined hereinabove, wherein the fluffy material is preferably a fluff of cellulosic fibers, and wherein the particles of the at least one superabsorbent polymer are preferably particles of a sodium acrylate copolymer.

Another possible embodiment of the invention relates to the method defined hereinabove, wherein the cellulosic fibers may consist of recycled cellulosic fibers, virgin cellulosic fibers, or may be a mix of recycled cellulosic fibers and virgin cellulosic fibers.

Another possible embodiment of the invention relates to the method defined hereinabove, wherein the fluffy material is a recycled fluffy material containing an amount of at least one jellying agent.

Another possible embodiment of the invention relates to the method defined hereinabove, wherein the recycled fluffy material are recycled cellulosic fibers obtained from industrial rejects of personal hygiene products such as incontinence briefs, baby diapers, women hygiene products, etc.

Another possible embodiment of the invention relates to the method defined hereinabove, wherein optionally, the recycled cellulosic fibers may further comprise particles of the at least one superabsorbent polymer (e.g. particles of at least one sodium acrylate copolymer), and optionally some impurities such as plastic materials.

Another possible embodiment of the invention relates to the method defined hereinabove, wherein the particles of the at least one superabsorbent polymer may be recycled particles of the at least one superabsorbent polymer obtained from industrial waste.

Another possible embodiment of the invention relates to the method defined hereinabove, wherein the particles of the at least one jellying material have an average diameter size varying from 50 μm to 500 μm, wherein the at least one absorption material represents from 2% by weight to 99% by weight, preferably from 40% by weight to 60% by weight, more preferably about 50% by weight, of the total weight of the at least one absorption material and the particles of the at least one jellying agent; and wherein the particles of the at least one jellying agent represents from 1% by weight to 98% by weight, preferably from 40% by weight to 60% by weight, more preferably about 50% by weight, of the total weight of at least one absorption material and the particles of at least one jellying agent.

Another possible embodiment of the invention relates to the method defined hereinabove, wherein the water-soluble material is made of at least one sheet of a water-soluble paper and/or is made of at least one film of a water-soluble polymer.

Another possible embodiment of the invention relates to the method defined hereinabove, wherein the at least one film of a water-soluble polymer has an inner surface, an outer surface and at least one opening allowing the water-based fluid to flow from the outer surface to the inner surface, and then contact the at least one absorption material and the at least one jellifying agent. Preferably, the at least one film of a water-soluble polymer may be provided with a plurality of openings.

Another possible embodiment of the invention relates to the method defined hereinabove, wherein the at least one water-soluble sheet of paper has an inner surface, an outer surface and at least one opening allowing the water-based fluid to flow from the outer surface to the inner surface, and then contact the at least one absorption material and the at least one jellifying agent. Preferably, the at least one water-soluble sheet of paper may be provided with a plurality of openings.

Another possible embodiment of the invention relates to methods as defined hereinabove where devices are provided with at least one opening, wherein said at least one opening are of any size and/or shape appropriate to allow water-based fluid to flow therethrough. As a non-limiting example, the at least one opening may have a diameter of about 0.045 inch. Also, preferably when a plurality of openings is provided, they can be distributed (randomly or according to a given pattern) on the surface of the device. As a non-limiting example, lines of openings may be provided with openings at about 0.25 inch from each other.

Another possible embodiment of the invention relates to the method defined hereinabove, wherein the water-soluble material is the film of the water-soluble polymer.

Another possible embodiment of the invention relates to the method defined hereinabove, wherein the film of the water-soluble polymer is a film of polyvinyl alcohol.

Another possible embodiment of the invention relates to the method defined hereinabove, wherein the container is formed around the at least one member with one film of a water-soluble polymer that is further thermo-sealable, and wherein the method further comprises a step for thermo-sealing together the periphery of the film or a portion of the film close of the periphery of the film.

Another possible embodiment of the invention relates to the method defined hereinabove, wherein the at least one container defines a pouch, a sachet, a bag or an envelope.

Another possible embodiment of the invention relates to a method for jellifying/absorbing a water-based fluid, said method comprising a step of contacting the device defined hereinabove, with the water-based fluid, said water-based fluid dissolving the water-soluble material and then being absorbed by the absorption material and reacting with the at least one jellifying agent to form a solid gel within the absorption material.

Another possible embodiment of the invention relates to a method for jellifying/absorbing a water-based fluid, said method comprising a step of contacting the water-based fluid with a device as defined hereinabove and provided with openings in the at least one container,
- a portion of said water-based fluid flowing through the openings to be absorbed by the absorption material and reacting with the at least one jellifying agent to form a solid gel within the absorption material, and
- a remaining portion of the water-based fluid dissolving the water-soluble material and then being absorbed by the absorption material and reacting with the at least one jellifying agent to form a solid gel within the absorption material.

Another possible embodiment of the invention relates to the method defined hereinabove for jellifying/absorbing a water-based fluid, said method further comprising a step of introducing the at least one device into a recipient adapted to collect the water-based fluid.

Another possible embodiment of the invention relates to the method defined hereinabove wherein the recipient is a bowl, basin or canister.

Another possible embodiment of the invention relates to the method defined hereinabove wherein the recipient is suction canister.

Another possible embodiment of the invention relates to the method defined hereinabove for jellifying/absorbing a water-based fluid, wherein the water-based fluid is a domestic water-based fluid, an industrial water-based fluid or a biological fluid, preferably a biological water-based fluid selected from the group consisting of blood, secretions, saliva, vomit, urine and feces, more preferably blood or urine.

Another possible embodiment of the invention relates to a use of at least one device as defined hereinabove, for jellifying/absorbing a water-based fluid, wherein the water-based fluid is a domestic water-based fluid, an industrial water-based fluid or a biological fluid, preferably a biological water-based fluid selected from the group consisting of blood, secretions, saliva, vomit, urine and feces, more preferably blood or urine.

Another possible embodiment of the invention relates to a use of on or more of the device as defined hereinabove, in combination with a suction canister for jellifying/absorbing a water-based fluid, wherein the water-based fluid is a domestic water-based fluid, an industrial water-based fluid or a biological fluid, preferably a biological water-based fluid selected from the group consisting of blood, secretions, saliva, vomit, urine and feces, more preferably blood or urine.

DETAILED DESCRIPTION OF THE INVENTION

In the following description, the same numerical references refer to similar elements. Furthermore, for the sake of simplicity and clarity, namely so as to not unduly burden the figures with several references numbers, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional, and are given for exemplification purposes only.

In addition, although the optional configurations as illustrated in the accompanying drawings comprises various components and although the optional configurations device as shown may consist of certain geometrical configurations as explained and illustrated herein, not all of these components and geometries are essential and thus should not be taken in their restrictive sense, i.e. should not be taken as to limit the scope of the present disclosure. It is to be understood that other suitable components and cooperations thereinbetween, as well as other suitable geometrical configurations the device, and corresponding parts, as briefly explained and as can be easily inferred herefrom, without departing from the scope of the disclosure.

Figure 1:
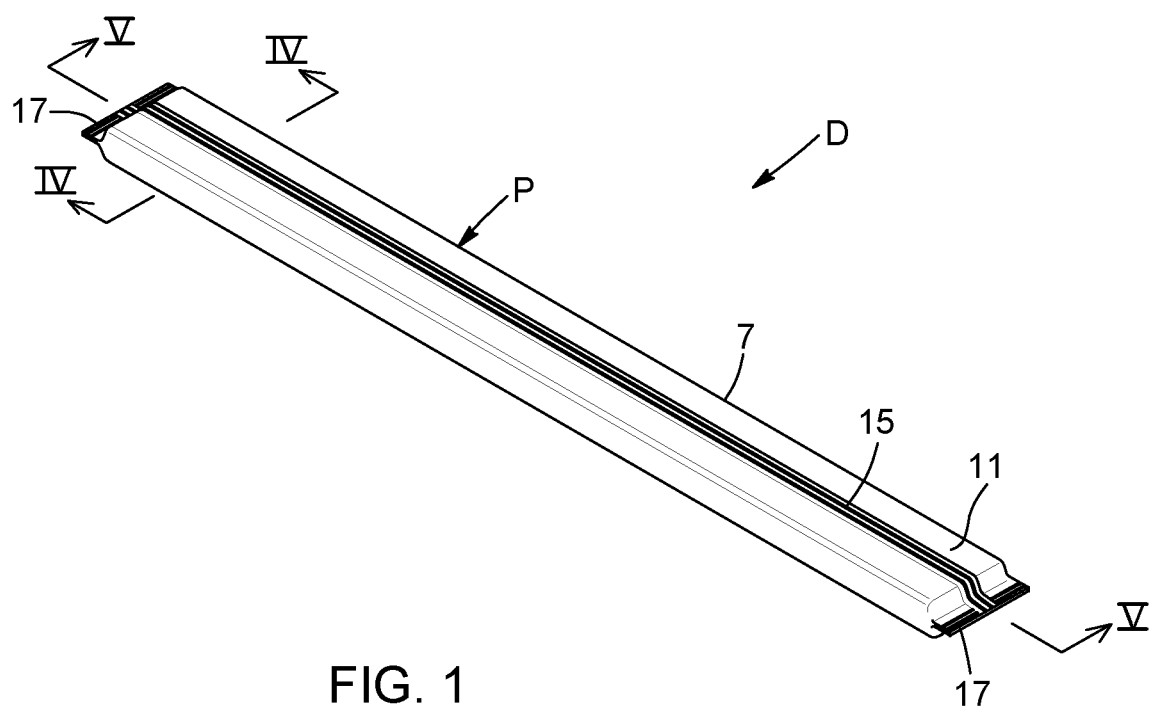
FIG. 1 represents a perspective view of a device according to the invention.
Figure 2:
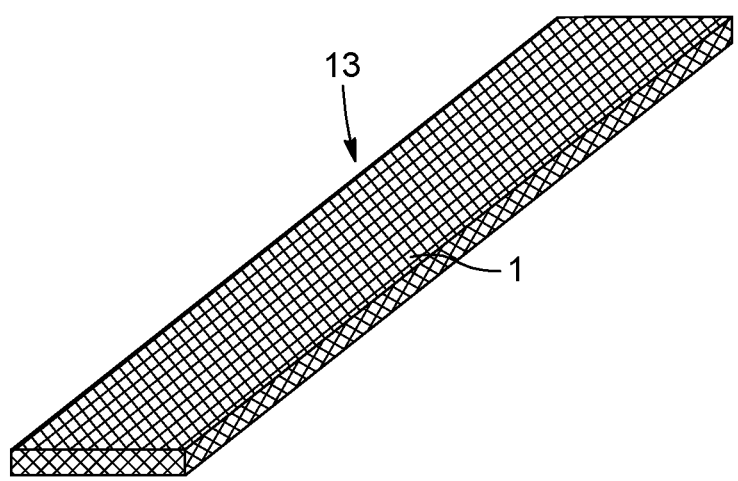
FIG. 2 represents a perspective view of the at least one member used in the device of FIG. 1.

With reference to FIG. 1, there is represented a device D according to one possible embodiment the invention. With reference to FIGS. 2 to 5, this device D comprising at least one stick 13, preferably as illustrated in FIGS. 1, 4 et 5, a stack of six sticks 13. Each stick 13 may comprise one member 1 (see FIG. 2) optionally supported on at least one support material, preferably, as illustrated in FIGS. 4 and 5, between layers 3 and 5, and a container 7.

According to another possible embodiment of the invention, the member 1 is a layer of a mixture comprising about 50% by weight of an absorption material and about 50% by weight of particles of at least one jellifying agent. Of course, the absorption material and the at least one jellifying agent may be of any source. According to another possible embodiment of the invention, the absorption material is a recycled cellulosic fluff and the at least one jellifying agent are particles of at least one sodium acrylate copolymer.

According to another possible embodiment, the container 7, with reference to FIG. 4, is made of one film 11 of polyvinyl alcohol. According to another possible embodiment of the invention, the film of polyvinyl alcohol may be of any appropriate thickness. Preferably, according to another possible embodiment of the invention, the film 11 is about 0.0015 inch thick. As illustrated in FIGS. 4 and 5, according to another possible embodiment of the invention, the film 11 is positioned around a stick 13 (preferably as illustrated in FIG. 4, a stack of six sticks 13), and has its periphery sealed together by any appropriate means (gluing, welding, etc.) commonly used in any flow wrapping processes, to form a pouch P. According to another possible embodiment of the invention, when the film is made of a thermo-sealable polymer (e.g. polyvinyl alcohol), the sealing of the periphery of the film 11 may be achieved by welding of opposite portions of the film according to a flow wrapping process. Flow wrapping processes and apparatus to carry out said processes are well known to persons skilled in the art and do not need to be further described.

Alternatively, the film 11 can be replaced by a water-soluble sheet of paper, preferably a tissue paper. In such a case, the periphery of the water-soluble sheet of paper may be joined together by gluing. Flow wrapping processes and apparatus to wrap the stick 13 (or preferably a stack of six sticks 13) with a water-soluble sheet of paper, including gluing of the periphery to join them together, are well known to persons skilled in the art and do not need to be further described.

More particularly, according to another possible embodiment of the invention, the device D can be manufactured according to a process comprising at least one of the following steps:

1. An absorption material and at least one jellifying agent are mixed together to provide a mixture. According to a preferred embodiment of the invention, a recycled cellulosic fluff and particles of sodium acrylate copolymer are mixed together to provide the mixture. Particles of the sodium acrylate copolymer are added to the recycled cellulosic fluff with a dosing device. Of course, if the recycled cellulosic fluff already contains particles of at least one jellifying agent (e.g. particles of at least one sodium acrylate copolymer), then only a complementary amount of the at least one jellifying agent will be added to the recycled cellulosic fluff with a dosing device. Any type of dosing devices can be used. Such dosing devices are well known to persons skilled in the art and do not need to be further detailed.

The mixture obtained can be shaped by any appropriate means well known to persons skilled in the art to define a layer of the mixture. Of course, the mixture can be shaped in various shapes according to techniques well known to persons skilled in the art.

Preferably, according to another possible embodiment of the invention, the recycled absorption material may be obtained from industrial rejects of personal hygiene products such as incontinence briefs, baby diapers, women hygiene products, and comprises recycled cellulosic fibers, optionally particles of at least one superabsorbent polymer (e.g. particles of at least one sodium acrylate copolymer), and optionally of plastic material (as impurities).

More preferably, according to another possible embodiment of the invention, virgin cellulosic fibers may be added to the recycled cellulosic fibers. Much more preferably, the virgin cellulosic fibers may have, as a non limitative example, the following features:

Average fibre length: 3.1 mm;
Network strength: 5.5. to 6.5 N;
Absorption time: 3.5 to 5.0 sec.; and
Absorption capacity: 9.5 to 10.5 g/g.

Optionally, according to another possible embodiment of the invention, the jellifying agent may be a recycled jellifying agent obtained from industrial wastes.

Also, according to another possible embodiment of the invention, the particles of at least one sodium acrylate copolymer may have a granulometry of varying from 75 to 500 micrometers with a volumetric mass varying from 400 to 700 kg/m$^3$. Optionally, according to another possible embodiment of the invention, the particles of the at least one sodium acrylate copolymer are recycled, particles obtained from industrial waste.

2. According to another possible embodiment of the invention, a layer of the mixture obtained from step 1 may be optionally laid against one layer of a supporting material, preferably between two parallel layers 3 and 5 of a sheet of a tissue papers, to form a multilayer assembly 18. Optionally, according to another possible embodiment of the invention, the multilayer assembly 18 may be further subjected to a calendering/heating step, to transform the multilayer assembly into a compressed multilayer assembly 19.

3. According to another embodiment of the invention, the multilayer assembly 18 or the compressed multilayer assembly 19 obtained from step 2, is then cut into a plurality of sticks 13 which are each provided with the member 1 sandwiched between layers 3 and 5 defined above. Of course, the cutting of the multilayer assembly 17 or the compressed multilayer assembly 19 can be carried out with any appropriate cutting tool well known to persons of having ordinary skills in the art, and cut into a large variety of forms. As an example, the compressed multilayer assembly may be cut with a guillotine knife to form a plurality of sticks 13.

Figure 3:
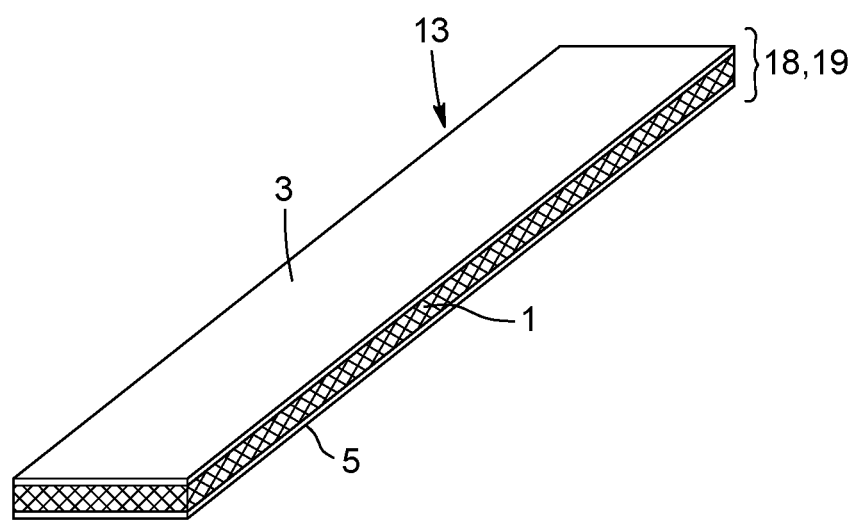
FIG. 3 represents a perspective view of the at least one member of FIG. 2 further provided with two layers of support material.
Figure 4:
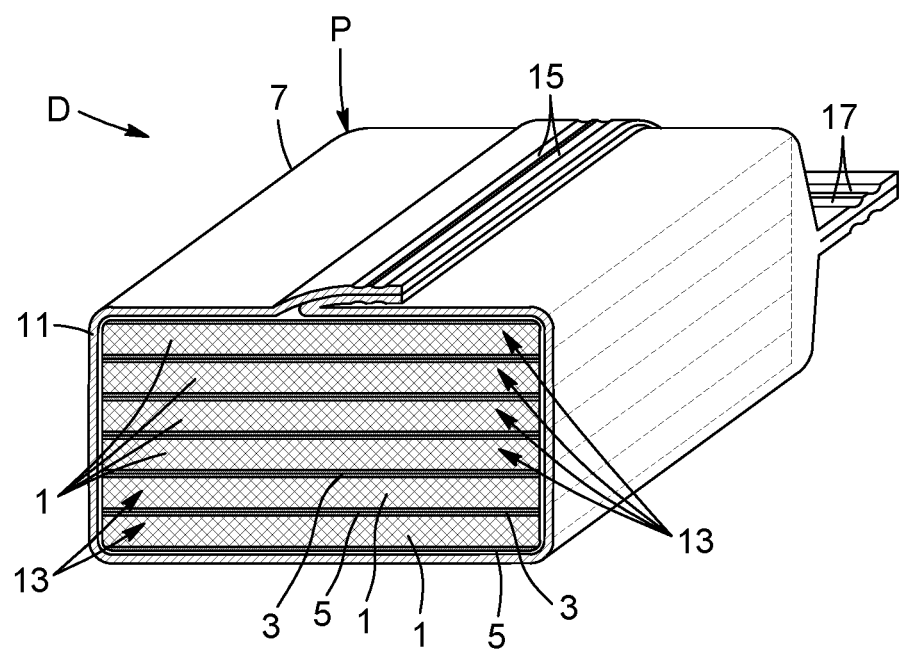
FIG. 4 represents a cross-sectional view according to line IV-IV in FIG. 1.
Figure 5:
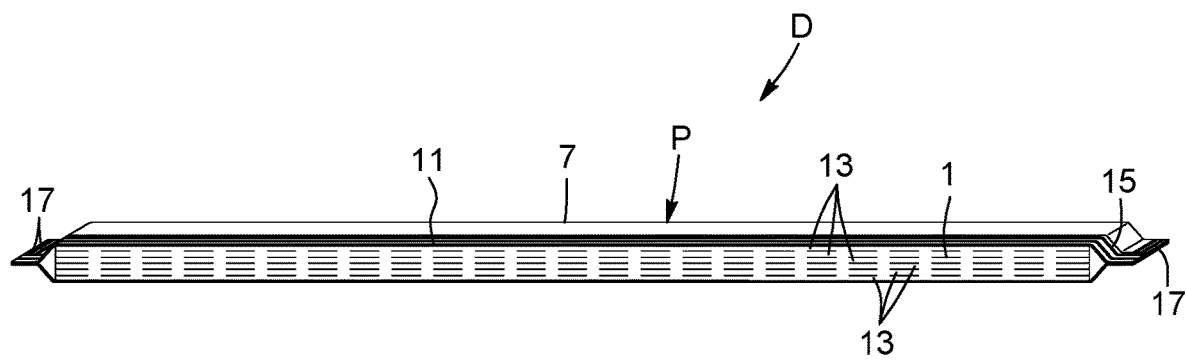
FIG. 5 represents a cross-sectional view according to line V-V in FIG. 1.

Referring to FIG. 3, according to another possible embodiment of the invention, each stick 13 may be provided with a member 1 and optionally with one or more layers of a supporting material, more particularly according to another possible embodiment, as illustrated in FIG. 4, between layers 3 and 5, as defined above. Preferably, according to another possible embodiment of the invention, the layers 3 and/or 5, more preferably layers 3 and 5, are each made of a sheet of tissue paper. Or course, any kind of sheet of tissue paper can be used. According to another possible embodiment of the invention, the sheet of tissue paper may have

- a basis weight varying from 15.5 to 17.1 g/m3,
- a MD stretch varying from 17 to 22%,
- a MD Tensile-Dry varying from 750 to 1050 g/inch,
- a CD Tensile-Dry varying from 200 to 390 g/inch, and
- a MD Tensile-Wet varying from 135 to 200 g/inch.

4. Optionally, according to another possible embodiment of the invention, as illustrated in FIGS. 4 and 5, a stack of sticks 13, more preferably a stack of six sticks 13, may be formed.

5. According to another possible embodiment of the invention, when using a conventional flow wrapping apparatus (not illustrated), a film 11 is positioned around the stick 13 or a stack of sticks 13, and portions the periphery of the film are sealed together by any appropriate technique well known to persons skilled in the art, to form the pouch P. Preferably, according to another possible embodiment of the invention, when the film 11 is made of a film of polyvinyl alcohol, any appropriate thermo-sealing techniques will known to persons skilled in the art can be used to joint portions of the longitudinal sides of the film with a longitudinal welding line 15, and joint portions of the ends sides of the film with end welding lines 17, to form the pouch P.

Alternatively, the film of polyvinyl alcohol can be replaced by a water-soluble sheet of paper, preferably a tissue paper. In such a case, the thermo-sealing techniques can be replaced by gluing techniques well known to persons skilled in the art.

According to another possible embodiment of the invention, when the device D is contacted with a water-based fluid (e.g. water, blood, urine, etc.), the water-soluble film of the container 7 (i.e. as illustrated in FIGS. 1, 4 and 5 the pouch P) starts dissolving and the mixture of the member 1 of the stick(s) 13 absorbs said water-based fluid which contacts the at least one jellifying agent to form a solid gel within the member 1.

According to another possible embodiment of the invention, when the pouch P is made of a film of polyvinyl alcohol, said pouch P starts dissolving in less than 10 seconds, and the mixture of the member 1 of the stick(s) 13 absorb said water-based fluid which contacts the particles of the at least one sodium acrylate co-polymer to form a solid gel within the member 1. It is to be noted that following the absorption and jellification of the water-based fluid, the member 1 of the device D swells and then bursts portions of the pouch P that are not dissolved yet.

Referring to FIGS. 1, 4 and 5, according to one possible embodiment of the invention, the device D comprises six sticks 13 contained in the pouch P made of a film of polyvinyl alcohol; is 25 cm long by 1.3 cm wide and 2 cm thick; and can absorb/solidified up to 600 ml of water in few seconds; after dissolution of the pouch P. Of course, the device D may be of various sizes and shapes. Alternatively, as another possible embodiment, the device D may be 13 cm long by 1.3 cm and 2 cm thick, and then absorb/solidified up to 300 ml of water in similar time frame.

Figure 6:
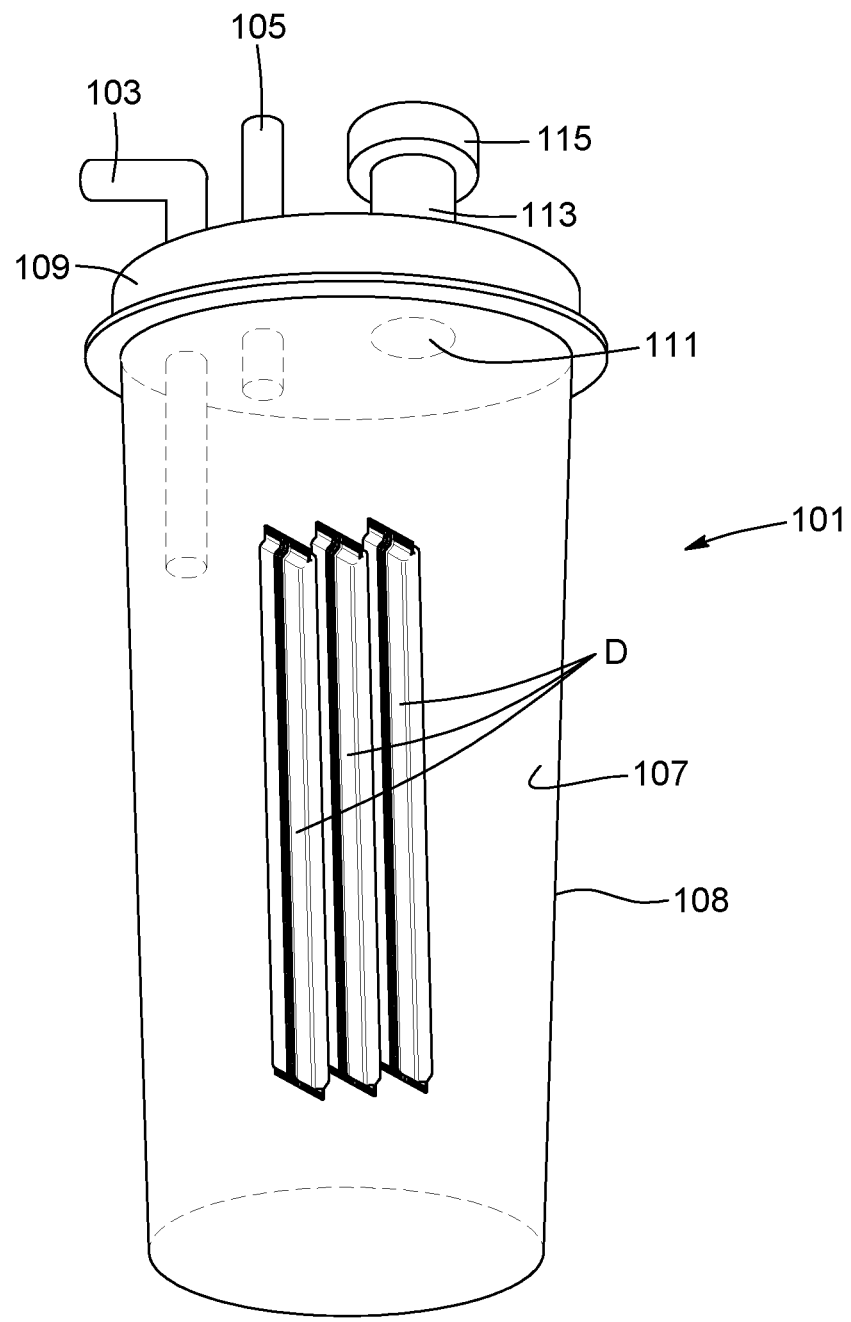
FIG. 6 represents an illustration of the device of FIG. 1 in a suction canister.

Referring to FIG. 6, there is illustrated a conventional suction canister 101 having an inlet 103 (adapted to be connected to an inlet tubing—not illustrated), an outlet 105 (adapted to be connected to an outlet tubing in fluid communication with a vacuum source—not illustrated), and a capacity 107 defined by a recipient 108, said capacity 107 being adapted for receiving water-based fluids (urine, blood, etc) and closed with a first lid 109.

The first lid 109 may be further provided with an opening 111, in fluid communication with a tubing 113 that can be removably closed with a second lid 115. The opening 111 and the tubing 113 is represented with in dotted lines.

In use, one or several devices D can be inserted in the capacity of the canister 101 either by removing the first lid 109 or via the opening 111 of the tubing 113.

Once the water-based fluid is absorbed and solidified within the member 1 of each stick 13, then the first lid 109 can be removed, and the content of the capacity 107 can be safely recovered by any appropriate means to be stored for further treatment before disposal, or disposed according to protocols required by regulations in force.

Figure 7:
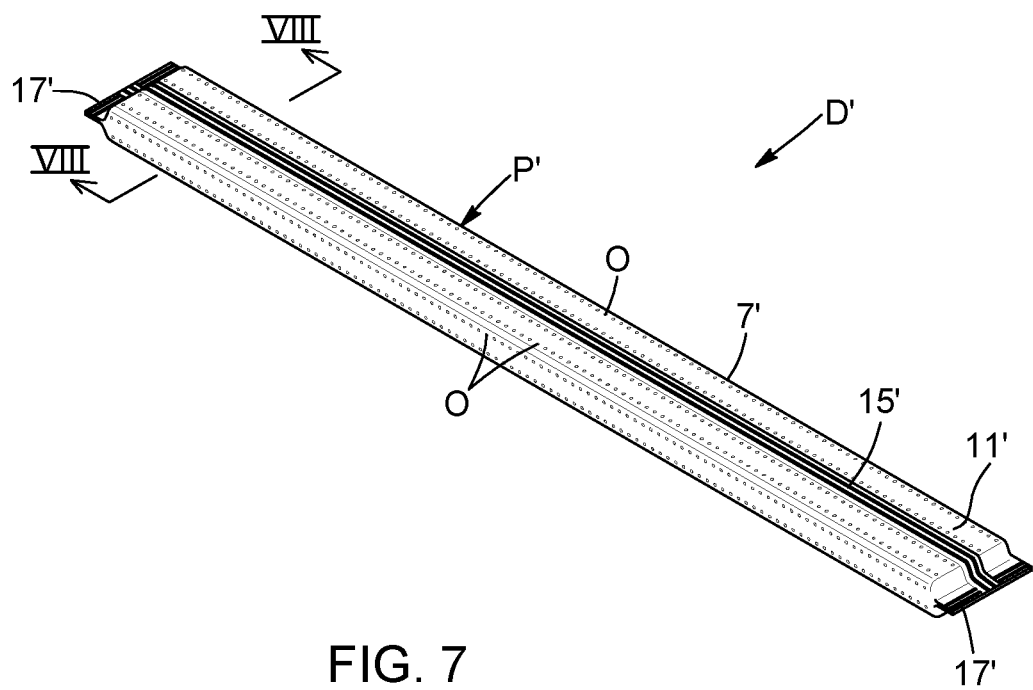
FIG. 7 represents a perspective a perspective view of a device according to the invention.
Figure 8:
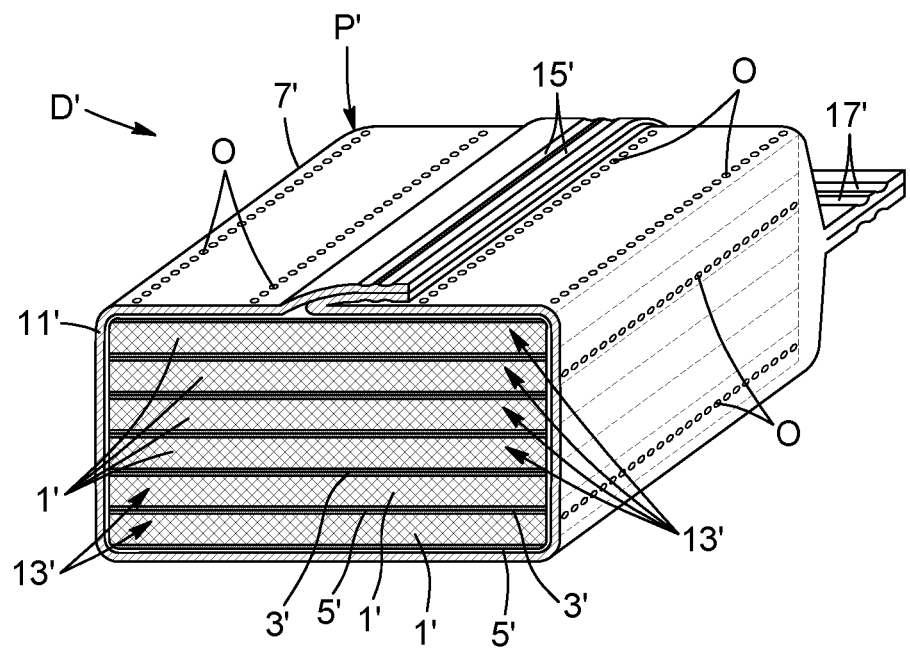
FIG. 8 represents a cross-sectional view according to line VIII-VIII in FIG. 7.

With reference to FIG. 7, there is represented another preferred embodiment of the invention. More particularly, FIG. 7 represents a device D' which is similar to the device D of FIG. 1 defined above, except as illustrated in FIG. 8, the container 7' is further provided with a plurality of openings O.

Also, as evidenced in the following example 1, this device D' surprisingly shows a rate of absorption/jellification that is substantially reduced with respect to rate of absorption/jellification of the device D.

Example 1

Three devices D and three devices D' were used. Devices D and D' are each 25 cm long by 1.3 cm wide and 2 cm thick.

Each device D is as defined in FIGS. 1, 4 and 5 and comprises six sticks 13 contained in the pouch P made of a film of polyvinyl alcohol having a thickness of about 0.0015 inch. The peripheric portions of the film are thermo-sealed together to form the pouch P according to usual techniques well known in the art (e.g. flow wrapping processes).

Each stick 13 is made from a mix comprising about 50 wt.-% recycled cellulosic fibers and about 50 wt. % of particles of a sodium acrylate copolymer (granulometry varying from 75 to 500 micrometers with a volumetric mass varying from 400 to 700 kg/m$^3$), provided between two layers of a water-soluble tissue paper (basis weight varying from 15.5 to 17.1 g/m3, MD stretch varying from 17 to 22%, MD Tensile-Dry varying from 750 to 1050 g/inch, CD Tensile-Dry varying from 200 to 390 g/inch, and MD Tensile-Wet varying from 135 to 200 g/inch).

Devices D and D' are identical except the devices D' are further provided on each longitudinal faces, with three lines of openings O. Each opening O has a diameter of about 0.045 inch. Openings O are spaced apart from each other at about 0.25 inch.

For the experimentation purposes, openings O were made in the film of polyvinyl alcohol a device D with a tool provided with a wheel having evenly spaced radiating sharp pins. Of course, for the industrial manufacturing of devices D' openings O can be provided in the film of polyvinyl alcohol either before or after the wrapping step, and with any industrial devices well known to persons skilled in the art.

Each devices D or D' was contacted with 600 ml of water at 38 C (to simulate the normal temperature of blood or urine) contained in a 1.3 L cylinder (to simulate usual size of suction canisters commonly used in hospitals). Each absorption test was filmed with a chronometer beside the cylinder to measure the bursting time of the device (i.e. the time at which the device bursts due to the swelling of the sticks 13) and the absorption time (i.e. the time required for the absorption of the water). The time starts when the device D or D' is dropped in the 1.3 L cylinder containing 600 ml of water.

Table showing examples of absorption results

| ABSORPTION RESULTS | | | | | | |
|---|---|---|---|---|---|---|
| | Device D (no openings) | | | Device D' (with openings) | | |
| Sample # | 1 | 2 | 3 | 4 | 5 | 6 |
| Bursting time (in sec.) | 13 | 19 | 9 | 2 | 3 | 2 |
| Absorption time (in sec.) | 64 | 62 | 62 | 61 | 59 | 66 |
| Total (in sec.) | 77 | 81 | 71 | 63 | 62 | 68 |

The results show that devices D' burst faster than devices D. More particularly, devices D' burst within an average of 2 seconds, while devices D burst within an average of 14 seconds. The absorption time (i.e. after the bursting time) is rather similar between devices D and D'. Also, it was noted that after being dropped in water, devices D first floated on the top of water before bursting and sinking at the bottom of the cylinder. However, devices D' quickly sunk in water toward the bottom of the cylinder.

Therefore, the total time required for absorbing water contained in the cylinder is shorter with devices D'.

It will be appreciated from the foregoing disclosure the scope of the claims should not be limited by the preferred embodiments set forth in the examples, but should be given the broadest interpretation consistent with the description as a whole.

The invention claimed is:

1. A device for the jellification/absorption of a water-based fluid, said device comprising:
   a) at least one member comprising at least one absorption material and at least one jellifying agent, and
   b) at least one container,
   wherein the at least one jellifying agent is adapted to react with the water-based fluid to form a gel;
   wherein the at least one member is contained within the at least one container, and
   wherein the at least one container is made, at least in part, of a water-soluble material.

2. The device according to claim 1, wherein the at least one absorption material is a fluffy material, wherein the at least one jellifying agent is in the form of particles, and wherein the fluffy material and the particles are mixed together to form a mixture, and wherein said mixture is shaped to form said at least one member.

3. The device according to claim 2, wherein the at least one member is further provided with at least one support material.

4. The device according to claim 3, wherein the at least one member corresponds to at least one layer of the mixture, and the at least one support material is at least one layer of the support material cooperating with the at least one layer of the mixture to form a multilayer assembly.

5. The device according to claim 3, wherein the at least one member corresponds to at least one layer of the mixture, and the at least one support material comprises two layers of the support material, each layer of the support material cooperating with the at least one layer of the mixture to form a multilayer assembly, and wherein the at least one layer of the mixture is positioned between the two layers of the support material.

6. The device according to claim 2, wherein the fluffy material comprises a fluff of recycled cellulosic fluff, wherein the particles of the at least one jellifying agent have an average diameter size varying from 50 µm to 500 µm; wherein the at least one absorption material represents from 2% by weight to 99% by weight of the total weight of the at least one absorption material and the particles of the at least one jellifying agent; and wherein the particles of the at least one jellifying agent represent from 1% by weight to 98% by weight of the total weight of at least one absorption material and the particles of the at least one jellifying agent.

7. The device according to claim 1, wherein the at least one container is made of at least one water-soluble sheet of paper and/or is made of at least one film of a water-soluble polymer, and wherein the at least one container has an inner surface, an outer surface and at least one opening allowing the water-based fluid to flow from the outer surface to the inner surface, and then contact the at least one absorption material and the at least one jellifying agent.

8. The device according to claim 7, wherein the at least one container is provided with a plurality of openings.

9. A method for the manufacture of the device defined in claim 1, wherein said method comprises a step of introducing one or more of the at least one member into the at least one container; or a step of forming the at least one container around the at least one member.

10. The method according to claim 9, wherein the at least one absorption material is a fluffy material, and wherein the at least one jellifying agent is in the form of particles, said method further comprising a step of mixing the fluffy material with the particles of the at least one jellifying agent to obtain a mixture, and a step of forming the mixture into the at least one member.

11. The method according to claim 10, wherein when the at least one member is further provided with at least one layer of a support material cooperating with the at least one member to form a multilayer assembly, said method further comprising a step of contacting the at least one member with the at least one layer of the support material.

12. The method according to claim 11, wherein the at least one member corresponds to at least one layer of the mixture, and wherein the at least one layer of the support material comprises two layers of the support material, each layer of the support material cooperating with the at least one layer of the mixture to form the multilayer assembly, and wherein the at least one layer of the mixture is positioned between the two layers of the support material.

13. The method according to claim 11, further comprising a step of compressing and optionally heating the multilayer assembly to provide a compressed assembly, wherein the at least one member corresponds to at least one layer of the mixture, and wherein the at least one layer of the support material cooperates with at least one layer of the mixture to form the compressed multilayer assembly.

14. The method according to claim 11, further comprising a step of compressing and optionally heating the multilayer assembly to provide a compressed assembly, wherein the at least one member corresponds to at least one layer of the mixture, wherein the at least one layer of the support material comprises two layers of the support material, each layer of the support material cooperating with the at least one layer of the mixture to form the compressed multilayer assembly, and wherein the at least one layer of the mixture is positioned between the two layers of the support material.

15. The method according to claim 11, wherein the fluffy material comprises a fluff of recycled cellulosic fluff, wherein the particles of the at least one jellifying agent have an average diameter size varying from 50 μm to 500 μm, wherein the at least one absorption material represents from 2% by weight to 99% by weight of the total weight of the at least one absorption material and the particles of the at least one jellifying agent; and wherein the particles of the at least one jellifying agent represents from 1% by weight to 98% by weight of the total weight of at least one absorption material and the particles of the at least one jellifying agent.

16. The method according to claim 9, wherein the at least one container is made of at least one water-soluble sheet of paper and/or is made of at least one film of a water-soluble polymer wherein the at least one container has an inner surface, an outer surface and at least one opening allowing the water-based fluid to flow from the outer surface to the inner surface, and then contact the at least one absorption material and the at least one jellifying agent.

17. The method according to claim 16, wherein the at least one container is provided with a plurality of openings.

18. The method according to claim 16, wherein the at least one container is made of at least one film of a water-soluble polymer and formed around the at least one member, wherein the water-soluble polymer that is further thermo-sealable, and wherein the method further comprises a step for thermo-sealing together the periphery of the at least one film or a portion of the at least one film close of the periphery of the at least one film.

19. A method for jellifying/absorbing a water-based fluid, said method comprising a step of contacting a device as defined in claim 1, with the water-based fluid, said water-based fluid dissolving the water-soluble material and then being absorbed by the absorption material and reacting with the at least one jellying agent to form a solid gel within the absorption material.

20. A method for jellifying/absorbing a water-based fluid, said method comprising a step of contacting the water-based fluid with a device as defined in claim 1 and provided with openings in the at least one container,
   a portion of said water-based fluid flowing through the openings to be absorbed by the absorption material and reacting with the at least one jellifying agent to form a solid gel within the absorption material, and
   a remaining portion of the water-based fluid dissolving the water-soluble material and then being absorbed by the absorption material and reacting with the at least one jellying agent to form a solid gel within the absorption material.

* * * * *